United States Patent
Bundy et al.

(10) Patent No.: US 9,642,935 B1
(45) Date of Patent: May 9, 2017

(54) SYNTHETIC, COMPOSITE OSTEOGENIC BONE GRAFT

(71) Applicants: Robert L. Bundy, The Woodlands, TX (US); Kevin P. Armstrong, Irvine, CA (US)

(72) Inventors: Robert L. Bundy, The Woodlands, TX (US); Kevin P. Armstrong, Irvine, CA (US)

( * ) Notice: Subject to any disclaimer, the term of this patent is extended or adjusted under 35 U.S.C. 154(b) by 0 days.

(21) Appl. No.: 13/752,326

(22) Filed: Jan. 28, 2013

Related U.S. Application Data

(60) Provisional application No. 61/591,784, filed on Jan. 27, 2012.

(51) Int. Cl.
  *A61L 27/22* (2006.01)
  *A61L 27/38* (2006.01)
  *A61L 27/58* (2006.01)

(52) U.S. Cl.
  CPC ......... *A61L 27/227* (2013.01); *A61L 27/3821* (2013.01); *A61L 27/3834* (2013.01); *A61L 27/58* (2013.01)

(58) Field of Classification Search
  None
  See application file for complete search history.

(56) References Cited

U.S. PATENT DOCUMENTS

| | | | |
|---|---|---|---|
| 6,454,811 B1 * | 9/2002 | Sherwood et al. | 623/23.76 |
| 6,887,488 B2 * | 5/2005 | Cui et al. | 424/426 |
| 8,101,268 B2 * | 1/2012 | Miles | A61L 27/10 264/604 |
| 2003/0031695 A1 * | 2/2003 | Kadiyala et al. | 424/423 |
| 2004/0131562 A1 * | 7/2004 | Gower et al. | 424/57 |
| 2006/0067969 A1 * | 3/2006 | Lu | A61L 27/3839 424/423 |
| 2006/0122706 A1 * | 6/2006 | Lo | A61L 27/10 623/23.5 |
| 2007/0098756 A1 * | 5/2007 | Behnam | 424/423 |
| 2008/0103605 A1 * | 5/2008 | Kadiyala et al. | 623/23.61 |
| 2010/0040668 A1 * | 2/2010 | Riman | A61K 31/12 424/426 |
| 2010/0055078 A1 * | 3/2010 | Hughes-Fulford | 424/93.7 |
| 2010/0247494 A1 * | 9/2010 | Gregory et al. | 424/93.7 |
| 2011/0182961 A1 * | 7/2011 | McKay | 424/423 |
| 2012/0003185 A1 * | 1/2012 | Meretzki | 424/93.3 |

OTHER PUBLICATIONS

Bronzino, Chapter 38, Tissue Engineering and Artificial Organs, The Biomedical Engineering Handbook, Third Edition, 2006.*
Dormer et al., Osteochondral Interface Tissue Engineering Using Macroscopic Gradients of Bioactive Signals, Ann Biomed Eng. Jun. 2010 ; 38(6): 2167-2182.*

* cited by examiner

*Primary Examiner* — Taeyoon Kim
*Assistant Examiner* — Srikanth Patury
(74) *Attorney, Agent, or Firm* — James A. Sheridan; Sheridan Law, LLC

(57) ABSTRACT

There is disclosed a synthetic, composite graft to support robust bone growth. In an embodiment, the synthetic, composite graft includes a synthetic scaffold material including a material resorbable through natural cellular processes; a signaling factor combined with the scaffold material; a cell adherence factor coated on the scaffold material; a quantity of viable bone forming cells adhered to the scaffold; and a matrix substrate binding the scaffold material. There is disclosed a method of forming a synthetic, composite graft to support bone growth for bone grafting. In one embodiment, the method includes providing a synthetic scaffold material including a material resorbable through natural cellular processes; combining a signaling factor with the scaffold material; coating a cell adherence factor on the scaffold material; adhering a quantity of viable bone forming cells to the scaffold; and encasing the scaffold material with a matrix substrate. Other embodiments are also disclosed.

5 Claims, 1 Drawing Sheet

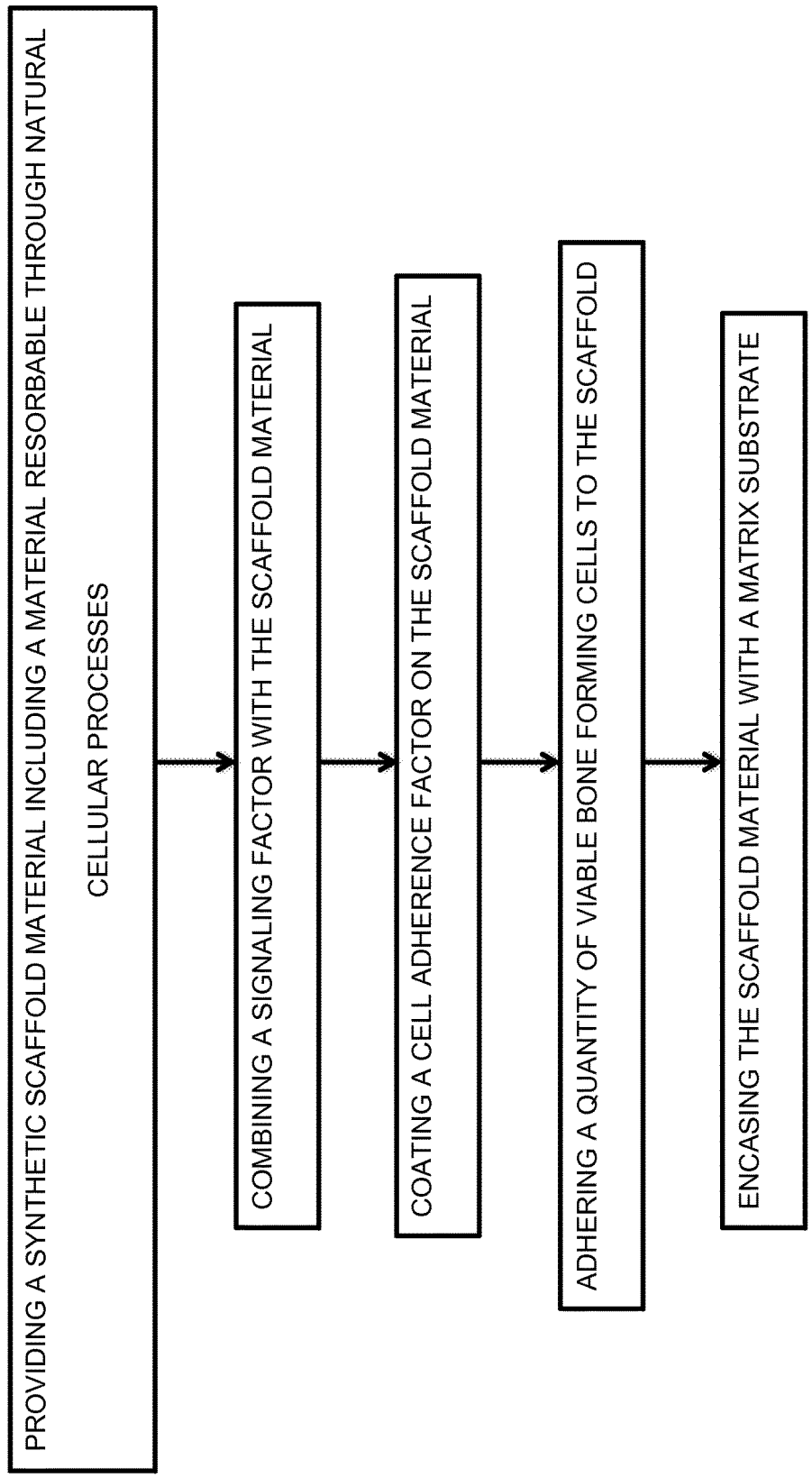

SYNTHETIC, COMPOSITE OSTEOGENIC BONE GRAFT

REFERENCE TO PENDING PRIOR PATENT APPLICATION

This application claims the benefit under 35 U.S.C. 119(e) of U.S. Provisional Patent Application No. 61/591,784, filed Jan. 27, 2012 by Robert L. Bundy, et al., for "SYNTHETIC, COMPOSITE OSTEOGENIC BONE GRAFT," which patent application is hereby incorporated herein by reference.

BACKGROUND

There has been much work done to create "synthetic autograft" and all have fallen short. Generally, a synthetic autograft includes a synthetic scaffold with various other graft materials.

SUMMARY

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

In an embodiment, there is provided a synthetic, composite graft to support robust bone growth, the synthetic, composite graft comprising a synthetic scaffold material including a material resorbable through natural cellular processes; a signaling factor combined with the scaffold material; a cell adherence factor coated on the scaffold material; a quantity of viable bone forming cells adhered to the scaffold; and a matrix substrate binding the scaffold material and/or particles.

In another embodiment, there is provided a synthetic, composite graft to support robust bone growth, the synthetic, composite graft comprising a synthetic scaffold material including a material resorbable through natural cellular processes a signaling factor combined with the scaffold material; and a quantity of viable bone forming cells adhered to the scaffold.

In yet another embodiment, there is provided a method of forming a synthetic, composite graft to support bone growth for bone grafting, the method comprising providing a synthetic scaffold material including a material resorbable through natural cellular processes; combining a signaling factor with the scaffold material; coating a cell adherence factor on the scaffold material; adhering a quantity of viable bone forming cells to the scaffold; and encasing the scaffold material with a matrix substrate.

In still another embodiment, there is provided a method of forming a synthetic, composite graft to support bone growth for bone grafting, the method comprising providing a synthetic scaffold material including a material resorbable through natural cellular processes; combining a signaling factor with the scaffold material; and adhering a quantity of viable bone forming cells to the scaffold.

In another embodiment, there is provided a synthetic, composite graft comprising a synthetic scaffold material having a signaling factor, a cell adherence factor, a quantity of viable bone forming cells, and a matrix substrate.

In still another embodiment, there is provided a synthetic, composite graft to support robust bone growth, the synthetic, composite graft comprising a synthetic scaffold material, a signaling factor, and a quantity of viable bone forming cells.

BRIEF DESCRIPTION OF THE DRAWINGS

Non-limiting and non-exhaustive embodiments of the present invention, including the preferred embodiment, are described with reference to the following FIGURE. Illustrative embodiments of the invention are illustrated in the drawing, in which:

The FIGURE illustrates an exemplary embodiment of a method of forming a synthetic, composite graft to support bone growth for bone grafting.

DETAILED DESCRIPTION

Embodiments are described more fully below in sufficient detail to enable those skilled in the art to practice the system and method. However, embodiments may be implemented in many different forms and should not be construed as being limited to the embodiments set forth herein. The following detailed description is, therefore, not to be taken in a limiting sense.

The present invention relates generally to bone grafts and, more specifically, it relates to a synthetic, composite osteogenic bone graft having the three elements needed for bone healing (i.e., osteoconduction, osteoinduction, and osteogenesis) in a form that will create an optimized microenvironment in a synthetic, off the shelf form.

In an embodiment, the bone graft includes a scaffold to guide the formation of bone healing, a matrix substrate to bind the graft together, a signaling element to induce the biological process of bone formation, a cell adherence factor to support the attachment of bone forming cells, and mesenchymal stem cells for osteogenesis.

There may be provided a synthetic, composite osteogenic bone graft having the three elements needed for bone healing by creating an advanced synthetic microenvironment.

In an embodiment, there is provided a synthetic, composite osteogenic bone graft incorporating all the key elements of autograft. These include incorporating an osteoconductive scaffold, osteinductive signal and osteogenic cells without the limitations of harvesting time and effort, donor site morbidity and available quantities.

Scaffold

In an embodiment, the synthetic, composite graft includes a synthetic scaffold readily made of available and suitable graft materials. For example, some graft materials may include, but not be limited to, any of the following: tri calcium phosphate, calcium sulfate, hydroxyapatite, hyaluronic acid, PLLA, PLGA, polycaprolactone, etc. The scaffold may be in a particle or block form together with an internal porosity appropriate to support the formation of bone by approximating the same essential morphology as bone. The manufacturing method of the scaffold can be any commercially available method capable of creating an appropriate structural characteristic as previously outlined including, but not limited to sintering, particle deposition, etc. In another embodiment, the particles may be solid having no inherent porosity and the intra-particulate space of the synthetic, composite graft can provide the needed porosity.

In an embodiment, there may be provided a three-dimensional scaffold with a matrix of interconnected pores in a range of sizes created in a material that is resorbable through natural cellular processes. Human bone is approximately 90% porous. Scaffolds in the range of 80 to 90% porosity have demonstrated to be appropriate for the purposes of tissue engineering. As such, porosity in this range may be used, but this range is not a limiting factor of the scaffold.

Matrix Substrate

The synthetic, composite graft may be bound together by a matrix substrate such that the synthetic, composite graft together with the matrix substrate may be formed into specific shapes for various implant applications. Such a suitable matrix substance might include, but is not limited to, collagen or similar and appropriate compound.

The matrix substrate may be of a material suitable to bind the particles together while allowing for the infiltration of fluid and cells, which support the bone healing process. The material may be inert and should be resorbable either through cellular activity or through dissolution. Materials that have shown to be suitable include collagen and hyaluronic acid, although other materials may be used as appropriate to bind together the synthetic, composite graft.

Signaling Element

The synthetic, composite graft may provide an inductive signal by incorporating a molecule, protein or growth factor suitable for this purpose or some combination of factors thereof. Such substances may include, but are not limited to, suitable bone morphogenic proteins (BMPs), transforming growth factor (TGF beta), platelet derived growth factor (pDGF), demineralized bone matrix (DBM), insulin like growth factor (IGF), etc.

The bone healing process is a complex interplay of cells, signaling factors and other molecules or elements, which results in the degradation of existing, non-viable bone and the creation of new bone in its place. There are number of signaling factors which participate in this process including, but not limited to, insulin like growth factors (IGF), transforming growth factor (TGF Beta), bone morphogenic proteins (BMPs), vascular epithelial growth factors (VEGF), demineralized bone matrix (DBM), etc. The synthetic, composite graft may incorporate one or a plurality of these growth factors to drive the bone healing process. They can be placed on the surface or within the scaffold lattice or on the scaffold lattice or within the matrix substrate as deemed appropriate.

Cell Adherence Factor

The synthetic, composite graft will include a cell adherence substance intended to promote enhance and expedite cell attraction on to the surface of the graft. Such substances may include, but are not limited to, fibronectin, bioactive glass, etc. These substances may be coated to the surface of the synthetic scaffold, incorporated into the latticework of the scaffold or blended into the matrix material holding the scaffold particles together.

Timely cell attachment is necessary to maintain cell viability and expedite the bone healing process. There are number of substances that play a role in creating a microenvironment supportive of attachment and viability of cells. One of the most common cell adherence substances is fibronectin. Bioactive glasses have also shown the ability to support cell attachment through an ionic exchange in the microenvironment. Hydroxyapatite has also shown to be an effective surface coating to promote cell adherence and bone growth. The synthetic, composite graft may incorporate fibronectin or other appropriate cell adherence material in the scaffold lattice, on the scaffold lattice, and/or within the matrix substrate.

Viable Bone Forming Cells

The synthetic, composite graft may have viable mesenchymal stem cells or osteoprogenitor cells from an autologous or allogeneic source adhered to the graft. These may be incorporated onto the scaffold itself or within the matrix substrate.

It is well documented that mesenchymal stem cells (MSCs) are the primary cell source for the formation of new bone. The ability of MSCs to self regenerate and differentiate into a variety of tissue types is useful in tissue engineering. There are a variety of tissue types which host a viable MSC population including muscle, bone marrow, fat, placenta, amniotic fluid, etc. Each of these tissue types possess an abundant quantity of mesenchymal stem cells. These cells can be isolated from autologous sources, allogeneic sources, or both.

Connections of Main Elements and Sub-Elements of Invention

As documented in various scientific literature, there are three elements necessary for bone to heal: osteoconduction, i.e., a scaffold to guide the formation of new bone, osteoinduction, i.e., the signal for the cells to grow new bone, and osteogenesis, i.e., the cells that remodel and deposit new bone. Removal or an imbalance in one of these three elements limits bone-healing response, quality and quantity. Autograft is the gold standard for bone grafting because of its three-dimensional osteoconductive scaffold, natural osteoinductive proteins/molecules and autologous cells for osteogenesis. There has been much work done to create "synthetic autograft" and all have fallen short, because these grafts fail to provide all three elements in a ready to use and reproducibly optimized form or quantity.

The optimum synthetic bone graft should maximize all these elements to create a microenvironment to support robust bone growth using the synthetic, composite graft. A scaffold may synergistically mimic the form and function of autologous bone with proven signaling molecules and mesenchymal stem cells known to be bone-forming cells. The cells must adhere to the scaffold. Synthetic scaffold materials have shown limited propensity to support expansive cell adherence and osteogenic activity. Fibronectin and similar coatings have been documented to create a surface environment supportive of cell attachment and is therefore included in the synthetic, composite graft. The scaffold particles may be formed for easy implantation so as to remain in the desired void. Incorporating a collagen substrate binds the particles together for handling and provides a microenvironment to support vascular and cellular infiltration.

Without order as a limiting factor, the manufacturing process for the synthetic, composite graft may include the following steps:

combine tri calcium phosphate (TCP) powder with signaling factors;

sinter TCP amalgam into porous particles;

coat the scaffold with fibronectin, bioactive glass or hydroxyapatite;

adhere isolated mesenchymal stem cells to the scaffold;

encase in collagen matrix in final form; and cryopreserve

A synthetic, composite osteogenic bone graft is disclosed having the three elements necessary for bone healing in a form to create an advanced synthetic microenvironment. The synthetic, composite osteogenic bone graft generally includes (1) an osteoconductive element, i.e., a scaffold to guide the formation of bone healing, (2) an osteoinductive element, i.e., a signaling element to induce the biological process of bone formation, and (3) an osteogenic element, i.e., mesenchymal stem cells for osteogenesis. In an embodiment, the synthetic, composite osteogenic bone graft may further include a matrix substrate to bind the graft together and a cell adherence factor to support the attachment of bone forming cells.

Although the above embodiments have been described in language that is specific to certain structures, elements, compositions, and methodological steps, it is to be understood that the technology defined in the appended claims is not necessarily limited to the specific structures, elements, compositions and/or steps described. Rather, the specific aspects and steps are described as forms of implementing the claimed technology. Since many embodiments of the technology can be practiced without departing from the spirit and scope of the invention, the invention resides in the claims hereinafter appended.

What is claimed is:

1. A synthetic, composite graft to support bone growth, the synthetic, composite graft comprising:
   porous particles formed by sintering a powder amalgam which is formed by combining a synthetic scaffold material and a signaling factor;
   wherein the synthetic scaffold material is tri-calcium phosphate;
   a cell adherence factor coated on the scaffold material;
   a quantity of viable bone forming cells adhered to the scaffold; and
   a matrix substrate encasing and binding the porous particles sintered into the scaffold material.

2. The synthetic, composite graft of claim 1, wherein the signaling factor includes at least one of bone morphogenic proteins (BMPs), transforming growth factor (TGF beta), platelet derived growth factor (pDGF), vascular epithelial growth factors (VEGF), demineralized bone matrix (DBM), and insulin like growth factor (IGF).

3. The synthetic, composite graft of claim 1, wherein the cell adherence factor includes at least one of fibronectin, bioactive glass, and hydroxyapatite.

4. The synthetic, composite graft of claim 1, wherein the quantity of viable bone forming cells includes mesenchymal stem cells (MSCs).

5. The synthetic, composite graft of claim 1, wherein the matrix substrate includes at least one of collagen and hyaluronic acid.

* * * * *